United States Patent [19]

Nielsen et al.

[11] 4,220,804

[45] Sep. 2, 1980

[54] SYNTHESIS OF GEM-DINITROALKANES

[75] Inventors: Arnold T. Nielsen, China Lake; Clifford D. Bedford, Claremont, both of Calif.

[73] Assignee: The United States of America as represented by the Secretary of the Navy, Washington, D.C.

[21] Appl. No.: 962,454

[22] Filed: Nov. 20, 1978

[51] Int. Cl.$^2$ .................. C07C 43/27; C07C 79/10
[52] U.S. Cl. ................................ 568/584; 568/932
[58] Field of Search ................. 149/105; 260/645; 568/584

[56] References Cited

U.S. PATENT DOCUMENTS

| | | | |
|---|---|---|---|
| 2,408,607 | 10/1946 | Buckley | 260/644 |
| 2,991,315 | 7/1961 | Plummer | 260/644 |
| 3,049,570 | 8/1962 | Plummer | 260/645 |
| 3,316,311 | 4/1967 | Plummer | 260/644 |
| 3,629,345 | 12/1971 | Harpell | 260/645 |

OTHER PUBLICATIONS

Novikov et al., Izvestiya Akademii Nauksssr, Otdelenie Khim. Nauk, No. 7, pp. 1295 to 1296 (1960).
Langercrantz et al., Acta. Chem. Scand., vol. 24, pp. 550 to 560 (1970).

*Primary Examiner*—Leland A. Sebastian
*Attorney, Agent, or Firm*—R. S. Sciascia; W. Thom Skeer; L. E. K. Pohl

[57] ABSTRACT

Substituted gem-dinitroalkanes are prepared by reacting a nitro olefin, tetranitromethane and an alcohol or organolithium derivative. The substituted gem-dinitroalkanes are useful as explosives, plasticizers and binders.

3 Claims, No Drawings

SYNTHESIS OF GEM-DINITROALKANES

BACKGROUND OF THE INVENTION

1. Field of the Invention

This invention relates to methods for the preparation of substituted gem-dinitroalkanes and to substituted novel gem-dinitroalkanes prepared by those methods.

2. Description of the Prior Art

The principle known methods for the preparation of gem-dinitroalkanes are (1) the Kaplan-Schechter reaction (oxidative nitration of mononitroalkanes with silver nitrate), (2) the Ponzio reaction (nitration of an oxime to the pseudonitrole followed by oxidation), (3) the ter Meer synthesis (halogenation of mononitroalkanes and displacement of the halide by nitrite) and (4) a method involving alkylation of alkali metal salts of aliphatic polynitro compounds. Each of these synthetic approaches has one or more shortcomings such as low yield and/or limited scope.

Substituted gem-dinitroalkanes prepared by the prior art methods have found use as explosives, plasticizers and binders. Accordingly, there is considerable interest in substituted new gem-dinitroalkanes and in new methods for their preparation.

SUMMARY OF THE INVENTION

This invention overcomes the shortcomings of the prior art by providing an easy to carry out method for producing, substituted, gem-dinitroalkanes from nitro olefins. The method provides for the introduction of two functional units to a nitro olefin in a one pot reaction. The method may be summarized by the following scheme.

SCHEME

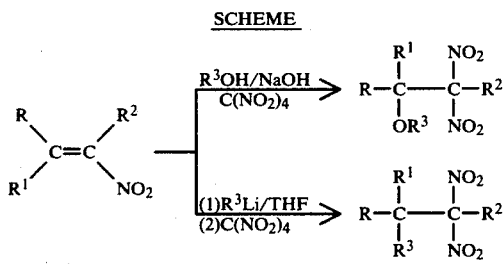

In the scheme, R is $C_6H_5$, $R^1$ is H, $R^2$ may be either H or $CH_3$ and $R^3$ may be an alkyl, alkenyl or aryl group. THF is an abbreviation for tetrahydroforan. Laboratory experimentation with the scheme has resulted in the preparation of several hereinafter specified new substituted gem-dinitroalkane compounds.

DESCRIPTION OF THE PREFERRED EMBODIMENT

It will be noted from the above scheme that either 2-alkoxy-gem-dinitroalkanes or substituted gem-dinitroalkanes having a carbon atom attached directly to a carbon atom of the starting compound may be prepared depending upon whether one uses $R^3OH$ or $R^3Li$. The examples set forth specific procedures which may be followed in carrying out each of the techniques. Example 1, which follows, sets forth procedures which may be used in preparing compounds having the formula:

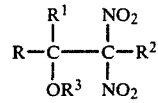

wherein R is $C_6H_5$, $R^1$ is H, $R^2$ is H and $R^3$ is alkyl, alkenyl or aryl. The example specifies the use of methanol and, therefore, the preparation of the compound wherein $R^3$ is $CH_3$. To produce compounds wherein $R^3$ is a different alkyl group, an alkenyl group or an aryl group, one merely substitutes the proper alcohol for methanol.

EXAMPLE 1

To an ice-cold solution of 4 g (0.10 mol) of NaOH dissolved in 10 ml of water and 20 ml of methanol was added dropwise a solution containing 7.5 g (0.05 mol) of ω-nitrostyrene and 9.8 g (0.05 mol) of tetranitromethane dissolved in 50 ml of methanol. The temperature during addition was maintained at 0°–10° C. The resulting mixture was stirred at ambient temperature for 1 hour after the addition was completed. The crude reaction mixture was then poured into 100 ml of water and acidified to pH 2 or less with concentrated HCl. The crude mixture was extracted twice with two 100 ml portions of diethyl ether, the combined ether extracts washed six to ten times with 100 ml portions of water, dried over anhydrous $MgSO_4$, and concentrated on a rotary evaporator at room temperature, affording 8.5 g (75% yield) of a reddish colored oil, essentially pure dinitro ether by NMR assay. The crude product was immediately dissolved in carbon tetrachloride to avoid possible fume-offs of residual nitroform, and chromatographed on 150 g of silica using carbon tetrachloride as eluent. The first fraction was analytically pure dinitro ether, 6.8 g (60% yield). The same procedure was also used in the preparation of compounds wherein $R^3$ was $CH_3CH_2$, $(CH_3)_2CH$ and $CH_2=CHCH_2$.

The following example sets forth, in detail, the procedure used in preparing 2-alkoxy-gem-dinitroalkanes, 2-alkanyloxy-gem-dinitroalkanes and 2-aryloxy-gem-dinitroalkanes wherein $R^2$ (see scheme) is $CH_3$.

EXAMPLE 2

1.15 g (0.05 mol) of sodium metal dissolved in 75 ml of methanol was added dropwise with cooling (0°–10° C.) a solution of 4.0 g (0.025 mol) of 2-nitro-1-phenyl-1-propene and 4.9 g (0.025 mol) of tetranitromethane in 25 ml of methanol. The resulting solution was stirred at room temperature for 1 hour. The product was isolated and purified as described in Example 1 above, except that acidification prior to workup was omitted. Ultimately there was obtained 2.5 g (42%) of analytically pure, white crystalline 2,2-dinitro-1-methoxy-1-phenyl-propane, mp 53°–55° C. The same procedure was employed to prepare the 2-ethoxy and 2-propoxy derivatives with the exception that the appropriate alcohol was substituted for methanol.

The preparation of dinitroalkanes having the structure:

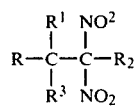

wherein R is $C_6H_5$, $R^1$ is H, $R_2$ is H or $CH_3$ and $R^3$ is alkyl, alkenyl or aryl is illustrated by the following example.

EXAMPLE 3

2,2-Dinitro-3-phenylbutane

To a solution of 4.03 g (0.025 mol) of 2-nitro-1-phenyl-1-propene dissolved in 30 ml of dry THF (cooled to −40° C. with an acetonitrile-dry ice bath) and under a positive nitrogen atmosphere was added with stirring 22 ml (0.05 mol) of a 5% ether solution of methyllithium. The resulting solution was stirred for 1 h at −40° C. followed by the addition of 4.9 g (0.025 mol) of tetranitromethane. The solution was then allowed to warm to room temperature and stirred an additional hour. The resulting product was isolated and purified as described in Example 1 above, yielding 3.4 g (60% yield) of an analytically pure white crystalline product, mp 76°–78° C. A similar procedure was used for the preparation of derivatives wherein $R_3$ (see structure above or scheme) was $CH_3(CH_2)_3$ and $R_2$ was H and wherein $R_3$ was $CH_3$ and $R_2$ was $CH_3$ (see scheme).

The compounds actually prepared in experiments leading to Examples 1 and 2, their boiling points or melting points and the yields obtained are summarized in the following table.

TABLE 1

| Compound | $R^1$ | $R^2$ | $R^3O$ | Yield/% | Bp/mp °C. |
|---|---|---|---|---|---|
| 1 | $C_6H_5$ | H | $CH_3O$ | 60 | 90 at 0.7 min |
| $2^a$ | $C_6H_5$ | H | $CH_3CH_2O$ | 44 | 29–30 |
| 3 | $C_6H_5$ | H | $(CH_3)_2CHO$ | 38 | b |
| 4 | $C_6H_5$ | H | $CH_2=CHCH_2O$ | 37 | b |
| 5 | $C_6H_5$ | $CH_3$ | $CH_3O$ | 42 | 53–55 |
| 6 | $C_6H_5$ | $CH_3$ | $CH_3CH_2O$ | 35 | b |
| 7 | $C_6H_5$ | $CH_3$ | $CH_3CH_2CH_2O$ | 20 | b |

[a]S. S. Novikov et al., Izvestiya Akademii Nauk SSSR, Otdelenie Khimicheskaya Nauk, 1295 (1960), teach preparation of this compound by addition of ethanol to ω,ω-dinitrostyrene.
[b]Obtained analytically pure as an oil column chromatography.

The compounds actually prepared in experiments leading to Example 3, their yields and their boiling point or melting points are summarized in the following table.

TABLE 2

| Compound | $R^1$ | $R^2$ | $R^3$ | Yield/% | Bp/mp/°C |
|---|---|---|---|---|---|
| 8 | $C_6H_5$ | $CH_3$ | $CH_3$ | 60 | 76–78 |
| 9 | $C_6H_5$ | H | $CH_3(CH_2)_3$ | 45 | d |
| $10^c$ | $C_6H_5$ | H | $CH_3$ | 29 | d |

[c]Lugercrantz et al., Acta Chemica Scandinavica, 24, 550 (1970) prepared compound 10 by a different method but gives no physical properties or details.
[d]Obtained analytically pure as an oil by column chromatography.

The compounds numbered 2 and 10 in the foregoing tables appear to have been prepared previously by methods different from those described herein. Compounds 1 and 3–9, on the other hand, have not, to the best of the inventors' knowledge, been prepared before.

What is claimed is:

1. A method for preparing compounds having the structure:

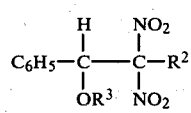

wherein $R^2$ is selected from the group consisting of H and $CH_3$ and wherein $R^3$ is selected from the group consisting of alkyl, alkenyl and aryl comprising the steps of:
 A. Forming a solution containing an alcohol having the formula $R^3OH$ wherein $R^3$ is selected from the group consisting of alkyl, alkenyl and aryl;
 B. adding an unsaturated compound selected from the group consisting of ω-nitrostyrene and 2-nitro-1-phenyl-1-propene and tetranitromethane to the solution; and
 C. allowing the unsaturated compound, the alcohol and the tetranitromethane to react.

2. A method for preparing a compound having the structure:

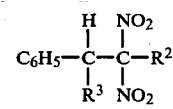

wherein $R^2$ is selected from the group consisting of H and $CH_3$ and wherein $R^3$ is selected from the group consisting of alkyl, alkenyl and aryl comprising the steps of:
 A. forming a solution containing a first compound having the structure:

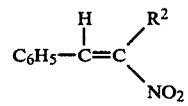

wherein $R^2$ is selected from the group consisting of H and $CH_3$;
 B. adding a lithium derivative having the formula $R^3Li$ wherein $R^3$ is selected from the group consisting of alkyl, alkenyl and aryl and tetranitromethane to the solution; and
 C. allowing said first compound, said lithium derivative and said tetranitramethane to react.

3. A compound having the structure:

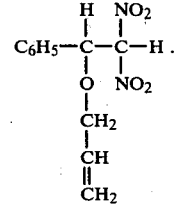

* * * * *